United States Patent [19]

Theodoru

[11] Patent Number: 5,720,299
[45] Date of Patent: Feb. 24, 1998

[54] METHOD FOR COLLECTING ENDOMETRIAL TISSUE SAMPLES WITH A SECURED HAND-HELD COLLECTING DEVICE

[76] Inventor: Liviu Theodoru, 1536, Summerhill avenue, app 5, Montréal (Québec), Canada, H3H 1B9

[21] Appl. No.: 531,758

[22] Filed: Sep. 21, 1995

[51] Int. Cl.⁶ .................................................. A61B 5/00
[52] U.S. Cl. .................................. 128/760; 604/317
[58] Field of Search .............................. 128/749, 752, 128/756–760; 604/317, 319, 128

[56] References Cited

U.S. PATENT DOCUMENTS

| | | | |
|---|---|---|---|
| 3,542,031 | 11/1970 | Taylor. | |
| 3,661,144 | 5/1972 | Gram. | |
| 3,774,613 | 11/1973 | Scitron. | |
| 3,855,997 | 12/1974 | Sauer | 128/760 |
| 3,863,624 | 2/1975 | Gram | 128/758 |
| 3,889,657 | 6/1975 | Baumgarten | 128/758 |
| 3,889,682 | 6/1975 | Denis. | |
| 3,946,739 | 3/1976 | Berman et al. | 604/128 |
| 4,257,425 | 3/1981 | Codman et al.. | |
| 5,045,074 | 9/1991 | Satterfield et al. | 604/317 |
| 5,217,024 | 6/1993 | Dorsey et al. | 128/749 |
| 5,458,138 | 10/1995 | Gajo | 604/319 |

FOREIGN PATENT DOCUMENTS 2063141  9/1993  Canada.

OTHER PUBLICATIONS

Commercial Brochure of "Serres" Suction Bag Products, Dated 1995, Manufactured By Muoviserres OY (Finland).

Primary Examiner—Max Hindenburg
Assistant Examiner—Pamela Y. Wingood
Attorney, Agent, or Firm—F. Martineau

[57] ABSTRACT

A hand held device comprising a sample collecting flask having a top mouth closed by a releasable closure cap, and defining a top sample inlet and a bottom air outlet. A first flexible rubber hose is removably plugged on the top inlet and is connected at its other end to a curette. A second flexible rubber hose is removably plugged on the bottom outlet and is serially connected to a vacuum pump assembly via a buffer container. A first rigid tube extends into the sample flask, being connected at one end to the top sample inlet, and opening into the sample flask spacedly proximate the bottom flooring of the sample flask. A second rigid tube also extends into the sample flask, being connected at one end to the bottom air outlet and opening into the sample flask spacedly proximate the closure cap. Therefore, the free extremities of the first and the second interior rigid tubes are vertically spaced apart. When the vacuum pump is activated, a negative pressure in the sample flask will be generated, producing a suction force in the curette for deposition of uterine wall fluid tissue sample inside the sample flask, exclusively of the air outlet hose.

3 Claims, 2 Drawing Sheets

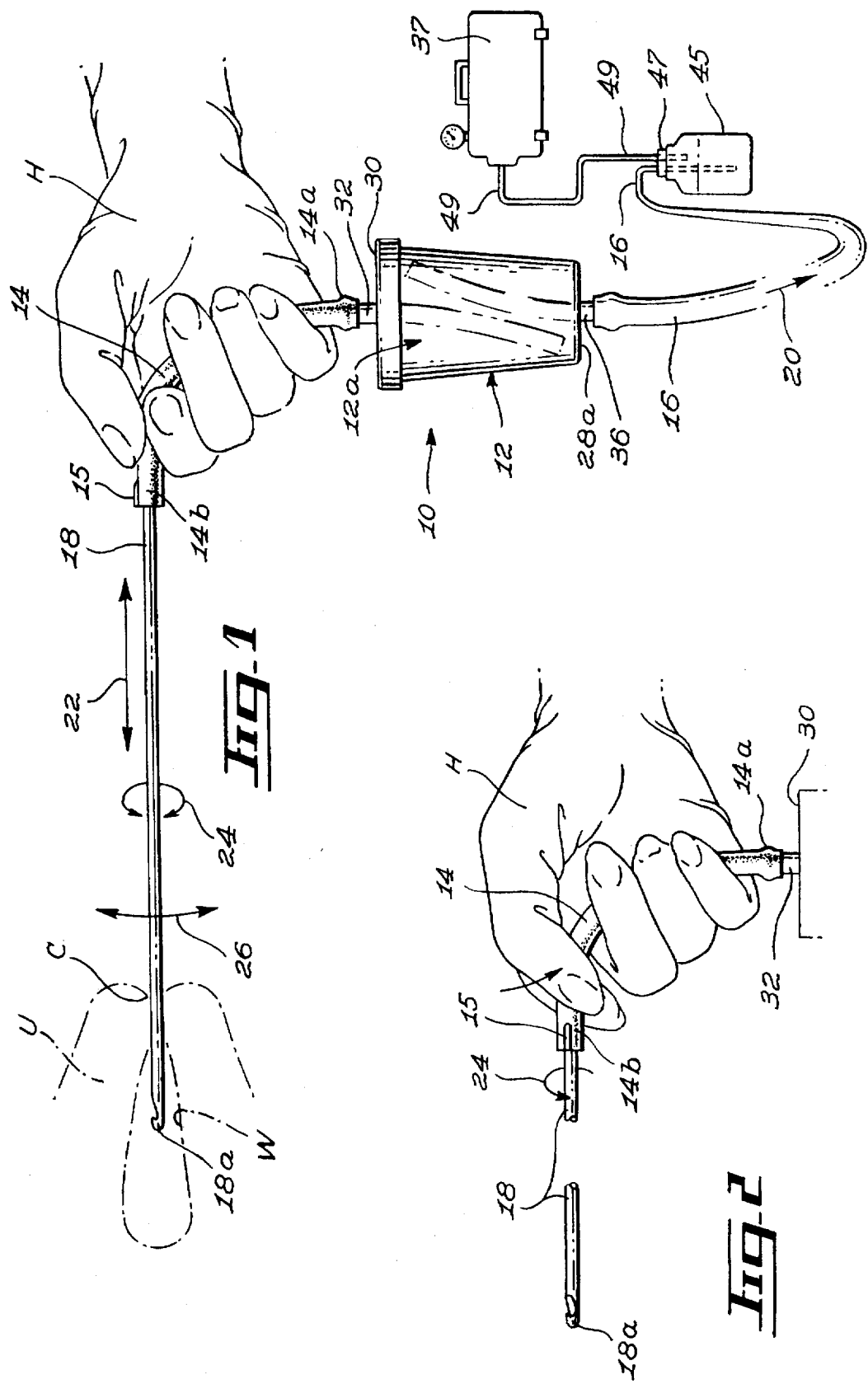

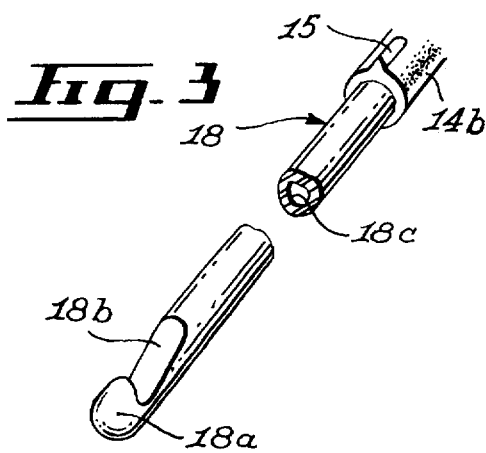
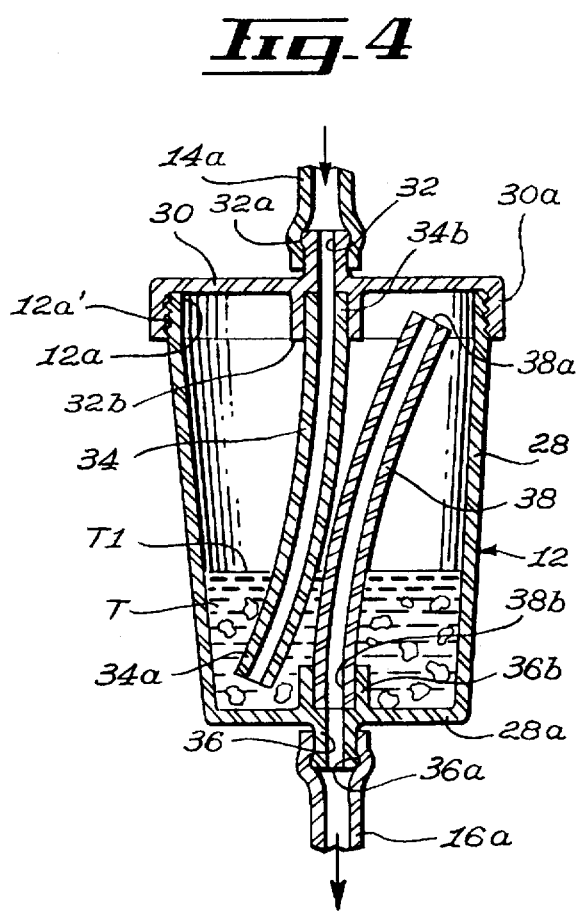
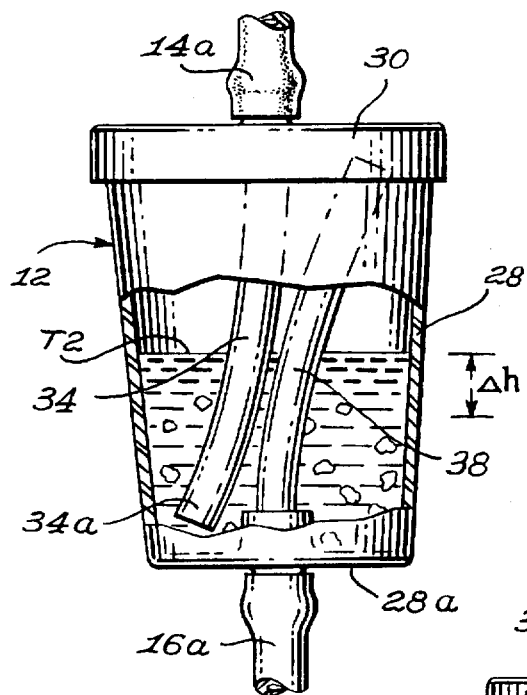
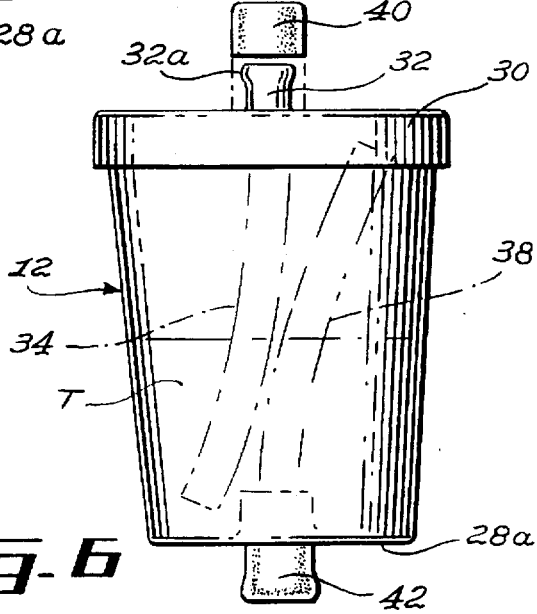

METHOD FOR COLLECTING ENDOMETRIAL TISSUE SAMPLES WITH A SECURED HAND-HELD COLLECTING DEVICE

CROSS-REFERENCE DATA

Disclosure document No 371,251 recorded 27 Feb., 1995 before the U.S. Patent and Trademark Office, is hereby incorporated by way of reference to the present patent application.

FIELD OF THE INVENTION

The present invention relates to devices used by medical practitioners in performing tissue sampling from the uterine endometrium of non anesthesized patients.

BACKGROUND OF THE INVENTION

Samples from the uterine wall are taken for a number of medical reasons, and more particularly for: emptying the uterine cavity, either following spontaneous incomplete abortion, prior to hysteroscopy, or during menorrhagia and metrorrhagia; detecting endometrial cancer; extracting the uterine menstrual content; bacterial culturing; etc. . . . There have been many apparatuses developed for this, to be used without anaesthesia on the patient.

Prior art shows that it is known to provide a collecting bottle or flask in which the samples are to be deposited. A curette is axially inserted into the uterus to capture and collect tissue samples from its inner wall, or endometrium, by rotating the curette and gently scraping the uterine wall with the sharp edge bevelled end mouth portion of the curette. This process is called curetting. The fluids and/or tissues flow from the uterus through the hollow curette and into the flask by means of a sample intake tube. Negative pressure is applied inside the flask through the instrumentality of a vacuum pump assembly connected to the flask or curette by means of a downstream air tube. This negative pressure is what sucks in the fluids and tissue from the uterus, into the curette, through the inlet tube and in the flask. Once the flask has gathered enough tissue and/or fluids, both tubes are removed from the flask. The flask cover is removed and a formaldehyde solution is poured through the flask top mouth to fixate the sampled cells and sterilize microbiological contaminants at the same time. The flask is then sealed at its top and bottom mouths, to be forwarded to a laboratory.

U.S. Pat. No. 3,542,031 issued in 1970 to M. B. TAYLOR shows such a system. The flask 26 has a closure 28 through which are inserted two rigid tubes 30 and 32. Both tubes extend through the top closure plug 28, and open at the upper portion of flask 26, near the bottom wall of closure 28 into a mesh basket 38.

U.S. Pat. No. 3,774,613 issued in 1973 to J. R. Woods is similar to the TAYLOR patent, in that both tubes (i.e. the tissue inflow tube and the vacuum pump tube) extend through the top closure plug and open at the upper portion of the bottle.

Such apparatuses have a major problem: the fluid flowing out of the sample intake tube usually reaches the access port of the air outlet tube, because both tube openings are so close to one another. When such fluid is sucked in by the air outlet tube, this tube air outlet become contaminated by the fluid.

This apparently simple task can be very dangerous for the medical staff in charge of such an operation. Indeed, blood and other bodily fluids may be contaminated by potentially contagious viruses, such as the HIV virus responsible for the deadly AIDS (Acquired Immuno Deficiency Syndrome) disease. The medical support staff in charge of cleansing the tubes and vacuum pump parts so infected, in between sample collections from successive patients, thus could expose themselves to these viruses. With the worldwide spreading of the HIV virus, it is getting to be a very important matter that all operations remain safe for the medical staff accomplishing them to prevent them from being contaminated in the midst of their job.

Another dangerous time period occurs when the flask cover is removed to open the flask mouth, to pour with a funnel member the formaldehyde solution to fixate the sampled material.

Another less dangerous, though more practical, problem with the prior art devices resides in the awkwardness of use of the sample collecting device by the medical practitioner. Some prior art references, such as U.S. Pat. No. 3,661,144 issued in 1972 to J. A. JENSEN and U.S. Pat. No. 4,257,425 issued in 1981 to J. P. RYAN, disclose collecting bottles rigidly linked with the curette. To efficiently capture tissue samples from the uterine wall, it is necessary to continuously rotate the curette back and forth to gently scrape the uterine wall: in doing so, the rigidly linked flask swings back and forth and the fluids inside the flask are shaken, thus increasing the likelihood that the fluids be prone to reach and get sucked into the outlet pump tube. This, as explained before, is highly undesirable, for it could expose the medical staff to contaminated blood when cleansing the pump tube.

Moreover, since the amount of collected sample material will decrease due to this loss to the outlet tube from the flask, and since the load in the sample flask is relatively small, the remaining load may become below the minimum threshold level required for satisfactory anatomo-pathology laboratory diagnosis.

The above-mentioned TAYLOR and WOODS patents have provided flexible inlet tubes that allow better manoeuvrability of the curette, but the proximity of their inlet and outlet tubes where they are plugged on the collecting bottle constrains them to provide a relatively long inlet tube: otherwise, the medical practitioner manipulating the inlet tube may accidentally hit the outlet tube with possibly important consequences (due to the contamination); if the outlet tube is securely fastened, it may still be in the way of the user of the device and therefore be cumbersome. Also, the considerable length of the sample intake tube results in the need of a much greater negative air pressure to counter the greater flow resistance offered by the flexible tube. Moreover, the chances of getting some tissue samples stuck in the inlet tube increase with the length of the tube. It is therefore undesirable to have a long inlet tube to overcome the problem that the inlet and outlet tubes are plugged close to one another on the collecting bottle.

OBJECTS OF THE INVENTION

It is the main object of this invention to provide an uterine sample collecting device in which the inlet curette-connected tube and the outlet vacuum pump tube are relatively positioned so as to prevent, as much as possible, any contamination of the interior of the outlet pump tube, and consequently to prevent the contamination of the medical staff coming in contact with the collecting device.

A further object of the invention is to eliminate the need to open the sample flask for pouring the sample fixation solution.

An important object of the invention is to substantially improve the efficiency, thoroughness, and handling finesse of medical acts by medical practitioners when performing uterine endometrium sampling.

An object is to facilitate the task of anatomopathology laboratory practitioners in retrieving tissue samples from the fixated and sterilized material in the sample collecting flask.

SUMMARY OF THE INVENTION

In accordance with the objects of the invention, there is disclosed a fluid sample collecting device for use in sampling endometrial tissues, comprising: (a) an elongated rigid fluid-tight pressure chamber, adapted to be hand-held vertically in an operative condition and including a top sample inlet and a bottom air outlet; (b) a first elongated flexible sample conveying hose member defining an inner end, sealingly mounted to said pressure chamber top inlet, and an outer end, adapted to be sealingly mounted to a sampling curette; (c) a second elongated flexible air hose member defining an inner end, sealingly mounted to said pressure chamber bottom outlet, and an outer end, adapted to sealingly fit a vacuum pump; (d) a first elongated tubular member defining a top end, sealingly mounted to said pressure chamber top inlet, and a bottom sample outlet port, opening inside said pressure chamber; and (e) a second elongated tubular member defining a bottom end, sealingly mounted to said pressure chamber bottom inlet, and a top air intake port, opening inside said pressure chamber; wherein said bottom sample outlet port and said top air intake port are spaced by a vertical gap of a value representing a large fraction of the total height of said vertically extending pressure chamber.

Preferably, there is provided tactile cue means, carried by said first hose member outer end and adapted to be in alignment with the outer mouth of the curette, for assisting the medical practitioner in continuously tracking the orientation of the curette outer mouth inside the uterus.

Said pressure chamber could include a large top mouth releasably sealingly closed by a flat closure cap member, said top sample inlet being mounted onto said closure cap member; and the pressure chamber could consist of a rigid bottle having a peripheral wall and a bottom flat flooring, said top sample inlet and said bottom air outlet being geometrically centred relative to said closure cap member and to said bottom flooring, respectively, wherein automatic vertical self-centering of said pressure chamber occurs whenever said first hose member is raised to hang said pressure chamber spacedly over ground.

Advantageously, said bottle is cross-sectionally cylindrical; and is preferably cross-sectionally frusto-conical, with said bottle top mouth being diametrally larger than said bottle bottom flooring.

The invention also concerns a method of collecting fluid sample from the endometrium of a uterus with a collecting device; said collecting device of the type comprising a rigid elongated pressure chamber including a top sample inlet and a bottom air outlet, a first flexible hose member defining an inner end sealingly mounted to said pressure chamber top inlet and an outer end sealingly mounted to a sampling curette, a second flexible hose member defining an inner end sealingly mounted to said pressure chamber bottom outlet and an outer end sealingly adapted to be fitted to a vacuum pump assembly, a first elongated tubular member defining a top end sealingly mounted to said pressure chamber top inlet and a bottom sample outlet port opening inside said pressure chamber, and a second elongated tubular member defining a bottom end sealingly mounted to said pressure chamber bottom inlet and a top air intake port opening inside said pressure chamber, said bottom sample outlet port and said top air intake port being spaced by a vertical gap of a value representing a large fraction of the total height of said elongated pressure chamber; wherein said method comprises the following steps: (a) grasping said first hose member and raising said pressure chamber spacedly over ground; (b) inserting the curette through the patient's cervix and into her uterine cavity; (c) powering the vacuum pump, to generate a negative pressure inside said pressure chamber; (d) manipulating said first hose member outer end for at least one of rotational, reciprocating, and tilting motions of the curette, to bring the curette outer end mouth in contact with various areas of the endometrial wall, wherein endometrial tissue and fluid samples are captured, collected, conveyed and deposited into said negative pressure chamber; (e) monitoring fluid sample intake in said negative pressure chamber to prevent build-up of said fluid sample beyond a first threshold level located well below said top air intake port; (f) withdrawing the curette from the uterine cavity; and (g) carrying said pressure chamber including the loaded tissue and fluid sample to a medical facility laboratory, for detailed anatomo-pathology analysis.

It is envisioned to add the following steps, occurring after step (f) but before step (g): (fa) inserting the curette outer half mouth portion vertically into an elongated container enclosing a tissue fixating and sterilizing solution, wherein the latter solution is aspirated and deposited into said negative pressure chamber and admixed with the collected endometrial fluid sample (the curette is now sterilized on the inside as well as the outside walls thereof, it can be released and discarded to the medical waste bin together with the first hose member); (fb) monitoring intake of said fixating and sterilizing solution to prevent build-up of the admixed compound of solution and fluid sample beyond a second threshold level located well below said top air intake port; and (fc) releasing said first and second hose members from said pressure chamber.

The following step should also be added, occurring after step (fc) but before step (g): sealing said top sample inlet and said bottom air outlet with closure plugs.

It is recommended to keep the flask in a vertical position when releasing said first and second hose members. Said top sample inlet is sealed first, and the flask can then be reversed for an easier fluid-proof plugging of said bottom air outlet.

BRIEF DESCRIPTION OF THE DRAWINGS

In the annexed drawings:

FIG. 1 is a side elevation of the uterine sample collecting device of the invention as held by a medical practitioner's hand, showing in phantom lines the cervix of the uterus and suggesting with arrows the manual movements of the curette;

FIG. 2 is a partial side elevation of the collecting device of FIG. 1, suggesting with arrows the corresponding rotation of the curette for a given rotation of the manoeuvring hose between the thumb and forefinger; hand;

FIG. 3 is a fragmented perspective view, at an enlarged scale, of the curette of FIGS. 1 and 2, and associated outer end portion of the manoeuvring flexible hose;

FIG. 4 is a vertical sectional view at an enlarged scale of the collecting flask of the device of FIG. 1, with a load of uterine tissue and fluid sample deposited inside the flask;

FIG. 5 is a partly sectional, fragmented elevation, at an enlarged scale, of the collecting flask of the device of FIG. 1, suggesting that tissue fixating fluid aspirated through the curette has been admixed with the initial load of uterine tissue and fluid sample; and FIG. 6 is an elevation, at an enlarged scale, of the collecting flask of the device of FIG. 1, the flexible inlet and outlet tubes being removed from the flask, the flask being ready for transport of the loaded flask to a medical facility laboratory for detailed sample analysis.

DETAILED DESCRIPTION OF THE EMBODIMENTS

The present invention is a hand-held sample collecting device for gathering tissue samples from the uterine wall without anaesthesia.

FIG. 1 shows, in phantom lines, the cervix C of a woman's uterus U, the latter defining an inner wall W or endometrium. A uterine sample collecting device 10 is provided according to the invention, comprising a collecting bottle or flask 12, having e.g. a capacity of about 90 milliliters (ml), for collecting a certain quantity of uterine tissue and fluids. Flask 12, which is preferably made from a transparent plastic material, consists of a main peripheral wall 28, a bottom flooring 28a, and a top open mouth 12a. A closure cap 30 releasably seals the top mouth 12a. The wall of flask 12 is preferably cross-sectionally circular, e.g. as illustrated slightly frusto-conical in shape, with the top mouth 12a being diametrally larger than the flooring 28a and the closure cap 30 being complementarily discoid and threadingly engaging by its inwardly threaded annular flange 30a the outwardly threaded edge portion 12a' of flask mouth 12a. However, other closure cap and flask shapes—e.g. cross-sectionally quadrangular—and other suitable cap to flask securing means—e.g. snap-fit interlock—would not be excluded from the scope of the invention.

For example, closure cap 30 could also include an annular rim, not illustrated, being mounted thereto in radially inwardly spaced fashion from the peripheral flange 30a; this annular rim being flexible and conical and complementary to the flask mouth 12a, wherein friction fit fluid-tight engagement can be achieved by progressive engagement of flask mouth 12a into the annular conical gap formed between cover flange 30a and said annular rim.

Closure cap 30 includes a central, integral, transversely outturned nipple 32a, and a coextensive, integral, transversely inturned nipple 32b, these nipples circumscribing a through-channel 32 for fluid communication into flask through the body of cap 30.

One end 14a of a flexible—preferably elastomeric—hose 14 is deformingly mounted sealingly against the radially outer wall of outturned rigid nipple 32a, while the opposite end thereof 14b is engaged by the inner end of an elongated, rigid (usually metallic) conventional curette 18. The interior cap nipple 32b is preferably diametrally enlarged relative to outer nipple 32a, so as to frictionally sealingly accommodate inside its cavity the top end 34b of an elongated, semi-rigid tube 34. The length of tube 34 is sized so that its bottom outlet end 34a be located very close to but spacedly from flask bottom flooring 28a. Flooring 28a includes a nipple arrangement similar to that of closure cap 30, comprising an inner, transverse, diametrally enlarged nipple 36b, an outer, transverse, diametrally smaller nipple 36a, these nipples circumscribing a through-channel 36 for air communication through the centre of flooring 28a and into flask 12.

Moreover, hose 14 is sized to be sufficiently elongated to allow rotation of the curette end 14b of hose 14, with the thumb and forefinger of a practitioner's hand H, while the remaining fingers of the same practitioner's hand H grasp firmly the sample flask end portion 14a of hose 14. That is to say, during rotation of hose end portion 14b, a torsional load is applied lengthwisely of hose 14, which will twist, since the opposite end portion 14a is not allowed to rotate. Accordingly, during rotation—and similarly during reciprocating motion—of hose end portion 14b, sample flask 12 will not rotate nor move fore and aft, thanks to the elasticity of the material of dampening hose 14. Usually, such a minimal length for rubber hose would be at least twelve centimeters (12 cm).

A semi-rigid tube 38 is frictionally sealingly engaged at its bottom end 38b into the cavity formed by inner nipple 36b, and is of a length sized so that its top inlet end 38a be located at the level of mouth 12a, very close to but spacedly from the main discoid wall of closed closure cap 30. Semi-rigid (or rigid) tubes 34, 38, should be arcuate, as illustrated, so as to diverge from one another inside flask 28 to axially clear one another (since inner nipples 32b, 36b are coaxial).

Another flexible, preferably elastomeric, hose 16 is deformingly sealingly engaged at its inner end 16a releasably around the radially outer wall of outer nipple 36a, and forms part of an air pump machine 37 by connecting to a second collecting flask 45, through the top closure plug 47 thereof. Flask 45 is connected by line 49 to air pump machine, and is usually concealed into the pump casing. Flask 45 may be of a conventional make, e.g. based on the concept disclosed in U.S. Pat. No. 3,542,031 to Taylor, supra, and does not form part of the invention as such. Flask 45 is conventionally used to shield pump machine 37 from accidental contamination—however unlikely—that could engage into tube 16. Hence, any contaminant accidentally escaping from main collecting bottle 12, through outlet port 36 and into downstream hose 16, would deposit into buffer flask 45; the pump 37 would not be reached by the contaminants. Since the medical practitioner must periodically monitor this transparent flask 45, any deposit therein will prompt the practitioner to shut off the pump. Arrow 20 in FIG. 1 suggests that air is sucked in from flask 12 into hose 16. Accordingly, flexible hoses 14 and 16 fluidingly communicate with the interior of flask 12 via tubes 34 and 38, respectively.

Hollow curette 18 conventionally has a free outer end mouth 18a, for retrieving samples from the uterine wall.

In operation, tissue sampling device 10 is to be operated single-handedly, as shown in FIG. 1. Indeed, with a single hand H, the medical practitioner firmly grasps inner end portion 14a of flexible sample hose 14, and with his thumb and forefinger engaging the hose portion distal end portion 14b where it overlaps the inner end of curette 18. By holding it there, the medical practitioner has a very good control over the movements of curette 18, as suggested in FIG. 1: thus, the medical practitioner can manually perform with curette 18 any one or a combination of the following movements: (a) an axial displacement (suggested by arrow 22); (b) an axial rotation (arrow 24); or (c) a tilting motion of free end 18a (arrow 26).

Flask 12 simply hangs from hose 14 in a vertical position; it will not rotate on itself as curette 18 is being axially rotated, since a torsional load will be enabled axially of flexible hose 14, and the same will be true as curette 18 is endwisely tilted and/or axially displaced, because curette 18 is linked to flask 12 by flexible hose 14, which allows curette 18 a relatively good freedom of movement without moving flask 12.

That flask 12 remains immobile is important, although not essential, in view of preventing leaks of tissue sample material therefrom. Thus, it would not be excluded from the scope of the method of use not to prevent rotation of the flask when finger rotating the upper hose 14. The three curette motions 22, 24, 26, can be performed in a fine adjustment manual mode, with wrist and fingers being solely involved, i.e. without any arm or forearm motion being required.

FIG. 2 shows how, with a twist of the thumb and forefinger of hand H, about hose distal portion 14b, curette 18 can be axially rotated to accomplish the circular curettage of the uterine wall, i.e. the basic function of curette 18. As discussed above, during this rotation, a torsional load is applied axially of elastic hose 14, so that distal hose portion 14b rotate, while proximal hose portion 14a does not, because the other three fingers of hand H anchor hose proximal end 14a to prevent axial rotation of bottle 12. The reader will appreciate the quantum leap in handling finesse achieved when curetting is performed by a medical practitioner.

FIG. 3 shows that free end 18a of curette 18 conventionally defines an elongated ovoidal bevelled end portion forming a sample intake mouth, 18b, having sharp edges that permit the user to scrape the superficial surface of wall W of uterus U when axially rotating curette 18, without injury to the uterus during cervix ingress of curette 18. FIG. 3 further shows that curette 18 defines an inner channel 18c merging with aperture 18b, in which the tissue samples will engage once dislodged from wall W by the edges of aperture 18b, during the curettage process. It is in lumen 18c that the uterine fluids are adapted to flow from uterus U to intake hose 14, before loading into flask 12 via tube 34 by depositing against flooring 28a.

Preferably, and as illustrated in particular in FIG. 3, a tactile cue means 15 is provided, e.g. a short axial end bulge, about hose outer end portion 14b. Tactile cue means 15 is in axial alignment with the ovoidal cutting edge mouth 18b of curette 18, to assist the medical practitioner in continuously feeling with his forefinger the relative orientation of the sharp cutting edges 18b of the opposite end of curette 18.

FIGS. 4 and 5 show collecting flask 12. Flask 12 defines a main body 28, being slightly frusto-conical, threaded at its upper end (corresponding to upper end 12a of flask 12) to be complementarily releasably engaged in a fluid-tight fashion by a threaded sealing closure cap 30.

In an alternate embodiment of the invention, not illustrated, inner tube 34 is integrally mounted to inturned nipple 32b of the flask closure cap 30 at its inner end 34b (which thus merges with nipple 32b); and inner tube 38 is integrally mounted to inturned nipple 36b of the flask flooring 28a at its outer end 38b (which thus merges with nipple 36b).

As suggested by the arrows in FIG. 4, the air pump 37 is serially connected to downstream hose 16 via assembly 45–49 (FIG. 1) will create a negative pressure chamber inside flask 28. Because of this negative pressure in chamber 28, fluid tissue samples from curette 18 and from hose 14 will be biased downwardly through tube 34 to deposit onto floor 28a, and this deposited fluid tissue material T will progressively build up and raise in level over flooring 28a to a given level T1 located well below top tube mouth 12a.

To gather uterine tissue and fluids in flask 12, curette 18 must first be inserted inside uterus U axially through cervix C. By powering the vacuum pump, air is drawn up in flask 12 through inner tube 38, through outlet through-channel 36 and into outlet hose 16 up to the pump, thus creating a negative pressure in flask 12. This negative pressure will cause a suction in first inner tube 34, transmitted in inlet through-channel 32, sample intake hose 14 and curette 18 to suck in all the desired fluids and tissue samples which have been scraped off—and collected from—the uterine wall W surface by curette free end 18a during the curettage process. The uterine fluids flowing in from first inner tube 34 are thus gathered in collecting flask 12. It is of course highly undesirable that the fluids reach the vacuum hose, for several reasons:

a) the tissue to be analyzed will be difficult to collect, since often, the sample volume is minimal and easily wasted; and most importantly, (b) the medical staff would have to manipulate this blood-stained material, which would expose them to being contaminated by one or more viruses in the uterine fluids, some of which could be very dangerous such as the HIV virus. It is therefore vitally important to keep the uterine fluids away from the top mouth 38a of second inner tube 38. Such fluid level monitoring of fluid T will easily be performed in real time fashion, simply by having the walls of flask 12 being made transparent, for see-through capability by the medical practitioner.

To accomplish this, it is necessary that flask 12 stay vertical at all times during the fluid collecting operation. Indeed, since the air intake port 38a is very close to top cap 30, if flask 12 is kept in an upright position with top cap 30 at the upper end, then flask 12 would have to be almost full for the uterine fluids to reach the level of top mouth 38a of second inner tube 38 and be sucked in. It is thus up to the medical practitioner in charge of the collecting operation to monitor collection of sample fluid and to stop filling flask 12 well before the fluid level inside flask 12 reaches the level of air intake port 38a. For example, the level of fluid in FIG. 4 being less than half the total inner volume of flask 12, e.g. 30% thereof, would be an approximately fairly safe level, which would constitute enough fluid to accomplish the medical testings—i.e. approximately 30 milliliters (ml) of fluid tissue sample for the suggested 90 ml total capacity of flask 12.

By holding collecting device 10 as suggested in FIGS. 1 and 2, i.e. leaving a certain free length of inlet hose 14 between hand H and flask 12, the latter will hang freely from inlet hose 14 and the gravity force will automatically pull flask 12 to a natural vertical position, given the freedom of movement conferred by flexible inlet hose 14. Indeed, flask 12, either filled with uterine fluid or not, simply hangs from sample intake hose 14 that acts as an axial support, the weight of flask 12 being uniformly and axially symmetrically distributed and hose 14 and air outlet hose 16 being coaxially attached thereon. All the forces acting on flask 12 are thus either axial forces or are counter-balanced by another force due to the axially symmetrical distribution of the weight of flask 12 and the weight of hose 16.

Self-centering of hoses 14 and 16 continuously occurs, in these circumstances, thanks to the geometrically central positioning of closure cap nipple 32a and of flooring nipple 36a. Therefore, when accomplishing the fluid collecting operation, the person doing so does not have to be concerned with adjusting the verticality of flask 12, since it will automatically perform self-centering to hang in an upright position.

Since first inner tube bottom end 34a is located near flooring 12b of flask 12, it is thus positioned far away from second inner tube top mouth 38a. This means that, if the protocol of operation of the present sample collecting device 10 is well followed, it would not be possible that the fluid flowing out of first inner tube 34 could in any way reach the second inner tube free end 38a and accidentally enter into tube 38.

Considering that vertical flask 12 will not normally be brought into any significant relative motion, since the curettage operation is performed by relative motion of flexible hose 14 which dampens motion to flask 12, and since the incoming fluid should not reach into second inner tube 38 towards the pump, no contamination of the outlet hose 16 assembly should occur by the uterine fluids. Thus, the medical staff will not have to expose themselves to the (possibly contaminated) fluids when cleansing said hose assembly 16.

Once the sample collecting operation is finished, curette 18 is released from the uterine cavity U, and brought into a bottle containing a tissue fixating and microbial sterilizing solution, e.g. a 10% solution of formaldehyde. From 20 to 30 ml of this formaldehyde solution is then sucked through curette mouth 18b into flask 12, with a slight negative pressure, since the vacuum pump has remained activated. The formaldehyde solution will fixate the sampled cells and will sterilize microbiological contaminants in the uterine tissue fluids, without the need for opening the flask 12. The level of the fluid inside flask 12 relative to level T1, will thus rise by a certain height Δh, to a second level T2, as shown in FIG. 5, e.g. to reach a level about half the total volume of flask 12; but the fluid level must positively remain well below the second tube air intake top mouth 38a.

After having introduced the formaldehyde solution into flask 12, both sample intake hose 14 and air outlet hose 16 are forcibly detached from nipples 32a and 36a, respectively, and thus from flask 12, making sure of keeping the latter in an upright position during this operation to prevent the fluid from flowing out from inlet and outlet through-channels 32 and 36. No leak should occur in these circumstances, provided the verticality of the flask 12 is maintained at all times by the medical practitioner, because the outlet port 38a remains above the highest fluid level T2.

As shown in FIG. 6, a first and a second fluid-tight caps 40 and 42 are then sealingly applied on lips 32a and 36a, respectively. The first outlet to be plugged will be the top nipple 32; then the flask 12 is overturned, to plug the bottom nipple 36. The fluid, trapped inside flask 12, can then be conveyed safely without regard to maintaining the verticality thereof, and forwarded to a medical facility laboratory for the proper anatomo-pathological examination to take place.

It is important to note that, at all times, the fluid remains inside flask 12, and that at no time did the medical staff come in contact with it. When it will have reached the laboratory, it will already have been sterilized by the formaldehyde solution so that all viruses and other microbial components will have been killed.

It is understood that even though, during this description, the implied use of the sample collecting device 10 was to gather uterine samples, it could just as well be used to empty the uterine cavity or any other similar use; only the size and volume of the collecting flask would need to be accordingly modified.

Alternately, if microbiological analysis is needed for the sample material, this material should not be fixated with formaldehyde, but rather with a non toxic solution such as physiological serum. Again, the reader will be able to appreciate the value of a sample containing flask that remains continuously sealed during handling thereof, with the micro-organisms being kept alive.

I claim:

1. A method of collecting fluid samples from the endometrium of an uterus with a collecting device; said collecting device of the type comprising a rigid elongated transparent pressure chamber bottle, including a top sample inlet and a bottom air outlet, a first flexible hose member defining an inner end portion sealingly mounted to said pressure chamber top inlet and an outer end portion sealingly mounted to a sampling curette, a second flexible hose member defining an inner end sealingly mounted to said pressure chamber bottom outlet and an outer end sealingly fitted to a vacuum pump and buffer flask assembly, a first elongated tubular member defining a top end sealingly mounted to said pressure chamber top inlet and a bottom sample outlet port opening inside said pressure chamber, and a second elongated tubular member defining a bottom end sealingly mounted to said pressure chamber bottle bottom inlet and a top air intake port opening inside said pressure chamber bottle, said bottom sample outlet port and said top air intake port being spaced by a vertical gap of a value representing a very large fraction of the total height of said elongated pressure chamber;

wherein said method comprises the following steps:

(a) grasping said first hose member and raising said pressure chamber spacedly over ground in a vertical condition;

(b) inserting the curette through the patient's cervix and into her uterine cavity;

(c) powering the vacuum pump, to generate a negative pressure inside said pressure chamber;

(d) manipulating said first hose member outer end portion with the thumb and forefinger of one hand for at least one of rotational, reciprocating, and tilting motions of the curette, while holding said first hose member inner end portion with the remaining fingers of the same said hand, to bring the curette outer end mouth in contact with various areas of the endometrial wall while the pressure chamber hangs over ground, wherein endometrial fluid samples are captured, collected, conveyed to and deposited into said pressure chamber;

(e) monitoring fluid sample intake in said pressure chamber to prevent build-up of said fluid sample beyond a first threshold level located well below said top air intake port;

(f) stopping the pump;

(g) withdrawing the curette from the uterine cavity;

(h) powering the pump (i) inserting the curette outer end mouth into a tissue fixating and sterilizing solution, wherein the latter solution is aspirated with very slight negative pressure and deposited into said pressure chamber and admixed with the collected endometrial fluid sample:

(j) monitoring intake of said fixating and sterilizing solution to prevent build-up of the admixed compound of solution and fluid sample beyond a second threshold level located well below said top air intake port;

(k) releasing said first and second hose members from said pressure chamber; and (l) carrying said pressure chamber including the loaded fluid sample to a medical facility laboratory, for detailed anatomopathology diagnosis.

2. A method of endometrial sampling as defined in claim 1, further including the following step, occurring after step k but before step l;

ka) sealing said top sample inlet with a closure plug;

kb) turning the pressure chamber upside down; and kc) sealing said bottom air outlet with a closure plug.

3. A sampling method as in claim 1, wherein in step (d), said first hose member inner end portion is firmly grasped by said remaining fingers of the hand, wherein said pressure chamber remains immobile during rotation of said first hose member outer end portion.

* * * * *